US010071052B2

(12) United States Patent
Woody

(10) Patent No.: US 10,071,052 B2
(45) Date of Patent: Sep. 11, 2018

(54) METHOD FOR THE PREVENTION AND TREATMENT OF ACNE

(71) Applicant: Avadim Technologies, Inc., Asheville, NC (US)

(72) Inventor: Stephen T. Woody, Asheville, NC (US)

(73) Assignee: AVADIM TECHNOLOGIES, INC., Asheville, NC (US)

( * ) Notice: Subject to any disclaimer, the term of this patent is extended or adjusted under 35 U.S.C. 154(b) by 0 days.

(21) Appl. No.: 14/946,299

(22) Filed: Nov. 19, 2015

(65) Prior Publication Data
US 2016/0184220 A1 Jun. 30, 2016

Related U.S. Application Data

(60) Provisional application No. 62/082,019, filed on Nov. 19, 2014.

(51) Int. Cl.
*A61Q 19/00* (2006.01)
*A61Q 19/10* (2006.01)
*A61K 9/00* (2006.01)
*A61K 8/42* (2006.01)
*A61K 8/64* (2006.01)
*A61K 8/19* (2006.01)
*A61K 9/08* (2006.01)
*A61K 38/02* (2006.01)
*A61P 17/10* (2006.01)

(52) U.S. Cl.
CPC .............. *A61K 9/0014* (2013.01); *A61K 8/19* (2013.01); *A61K 8/42* (2013.01); *A61K 8/64* (2013.01); *A61K 9/08* (2013.01); *A61K 38/02* (2013.01); *A61Q 19/00* (2013.01); *A61Q 19/10* (2013.01); *A61K 2800/28* (2013.01); *A61K 2800/884* (2013.01)

(58) Field of Classification Search
None
See application file for complete search history.

(56) References Cited

U.S. PATENT DOCUMENTS

| 3,557,006 | A | * | 1/1971 | Dalby | C11D 9/14 |
| | | | | | 510/146 |
| 4,784,647 | A | | 11/1988 | Gross | |
| 5,702,992 | A | | 12/1997 | Martin et al. | |
| 5,902,283 | A | | 5/1999 | Darouiche et al. | |
| 6,231,875 | B1 | | 5/2001 | Sun et al. | |
| 6,358,516 | B1 | * | 3/2002 | Harod | A61K 8/0208 |
| | | | | | 424/401 |
| 6,498,157 | B2 | | 12/2002 | Sodemann | |
| 7,635,358 | B2 | | 12/2009 | Tan | |
| 7,947,021 | B2 | | 5/2011 | Bourne et al. | |
| 8,127,922 | B2 | | 3/2012 | Nordholm et al. | |
| 8,328,792 | B2 | | 12/2012 | Nishtala et al. | |
| 8,414,547 | B2 | | 4/2013 | DiFiore et al. | |
| 9,446,090 | B2 | | 9/2016 | Bevilacqua et al. | |

| 2002/0058010 | A1 | * | 5/2002 | Picard-Lesboueyries | |
| | | | | | A61K 8/0295 |
| | | | | | 424/43 |
| 2002/0103092 | A1 | * | 8/2002 | Tashjian | A61K 8/347 |
| | | | | | 510/130 |
| 2007/0071705 | A1 | * | 3/2007 | De Oliveira | A61K 9/0014 |
| | | | | | 424/70.13 |
| 2007/0212381 | A1 | | 9/2007 | DiFiore et al. | |
| 2007/0244449 | A1 | | 10/2007 | Najafi et al. | |
| 2009/0221989 | A1 | | 9/2009 | Najafi et al. | |
| 2010/0096287 | A1 | | 4/2010 | Stoesz et al. | |
| 2010/0145251 | A1 | | 6/2010 | Polaschegg | |
| 2010/0209535 | A1 | | 8/2010 | Kiani | |
| 2010/0311668 | A1 | | 12/2010 | Farwick et al. | |
| 2011/0033540 | A1 | | 2/2011 | Daniloff et al. | |
| 2011/0129552 | A1 | | 6/2011 | Saha et al. | |

(Continued)

FOREIGN PATENT DOCUMENTS

| GB | 2481456 A | 12/2011 | |
| GB | 2511350 A | 9/2014 | |
| WO | WO 2013142374 A1 * | 9/2013 | ............. A61K 38/16 |

OTHER PUBLICATIONS

Tambyah et al.,"The Direct Costs of Nosocomial Catheter-Associated Urinary Tract Infection in the Era of Managed Care", Infection Control & Hospital Epidemiology, vol. 23, Issue 1, Jan. 2002, pp. 27-31.
Kawasaki City College of Nursing Repository Bulletin, vol. 12, No. 1, 2007, pp. 17-25.
Mosley et al., "Sterilization and Estimates", Pharmaceutical Microbiology Forum Newsletter, vol. 14, Issue 5, May 2008, pp. 1-15.
Lo et al., "Strategies to Prevent Catheter-Associated Urinary Tract Infections in Acute Care Hospitals", Infection Control and Hospital Epidemiology, vol. 29, Supplement 1, Oct. 2008, p. S41.
Gould et al., "Guideline for Prevention of Catheter-associated Urinary Tract Infections", Centers for Disease Control, Healthcare Infection Control Practices Advisory Committee, 2009, p. 8, 9; Q2B.1.a; p. 39 (Total 67 pages).

(Continued)

*Primary Examiner* — Robert T. Crow
*Assistant Examiner* — John P Nguyen
(74) *Attorney, Agent, or Firm* — Pedigo Law Firm PLLC; Paul Pedigo; Heather Medd Seitz

(57) ABSTRACT

A system for treating and preventing multiple forms of acne includes applying a solution to the skin to assist maintaining the skin's natural acidic mantle of 4.0 to 6.5, preserve moisture transport properties, and maintain specialized lipid content, allowing the skin to function normally, and assisting the skin to heal wounds caused by acne and associated bacterial infections. The method steps include one or more of the following: applying the formulation with surfactants incorporated therein to the skin as a cleanser, rinsing with water; applying the solution, with or without surfactants, and allowing the solution to air dry; repeating the applications and allowing them to air dry throughout the day; and repeating the cleansing and rinsing steps and applying the solution and allowing to air dry before retiring. One or more of the method steps may be repeated on a continual basis, typically daily, for an extended period of time.

15 Claims, 1 Drawing Sheet

(56) References Cited

U.S. PATENT DOCUMENTS

| | | | |
|---|---|---|---|
| 2011/0245757 A1* | 10/2011 | Myntti | A61K 31/19 604/22 |
| 2011/0262558 A1 | 10/2011 | Huckfeldt et al. | |
| 2011/0283662 A1 | 11/2011 | Zhang et al. | |
| 2012/0203211 A1 | 8/2012 | Weadock et al. | |
| 2012/0282348 A1 | 11/2012 | Yates et al. | |
| 2012/0282351 A1 | 11/2012 | Najafi et al. | |
| 2013/0006226 A1 | 1/2013 | Hong et al. | |
| 2013/0085093 A1 | 4/2013 | Ishihara et al. | |
| 2013/0085469 A1 | 4/2013 | Polaschegg | |
| 2013/0123221 A1* | 5/2013 | Pearlman | A61K 31/58 514/171 |
| 2014/0179640 A1* | 6/2014 | Weinberger | A61K 31/194 514/159 |
| 2015/0343172 A1 | 12/2015 | Woody | |
| 2016/0158393 A1* | 6/2016 | Woody | A61L 2/0088 514/390 |
| 2017/0128600 A1 | 5/2017 | Woody | |

OTHER PUBLICATIONS

Burnett et al., "Stategies to Prevent Urinary Tract Infection from Urinary Catheter Insertion in the Emergency Department", Journal of Emergency Nursing, Dec. 9, 2009, 548 Pages.

Mintel GNPD, "Acne Scar Reduction System", Dermajuv, Feb. 1, 2010, pp. 1-9.

Vanderbilt University, "VUMC Guidelines for Management of Indwelling Urinary Catheters", Vanderbilt University Medical Center, Jun. 3, 2010, 5 Pages.

Centers for Disease Control and Prevention, "Technical Information—HAI and Antibiotic Use Prevalence Survey", Emerging Infections Program—Healthcare-associated Infections Projects, 2014, 3 pages.

Cantrell, Susan, "Sharing Successes Paves the Road to Higher-Quality Healthcare", HealthCare Purchasing News, Available online at <https://www.hpnonline.com/ inside/2014-04/1404-IP-Success.html>, Apr. 2014, 8 pages.

Magill et al., "Multistate Point-Prevalence Survey of Health Care-Associated Infections", The New England Journal of Medicine, vol. 370, No. 13, Published on Mar. 27, 2014, pp. 1198-1208.

Schauer et al., "Bariatric Surgery Versus Intensive Medical Therapy for Diabetes—3-Year Outcomes", The New England Journal of Medicine, vol. 370, Issue 21, Mar. 31, 2014, pp. 2002-2013.

Zeuzem et al., "Sofosbuvir and Ribavirin in HCV Genotypes 2 and 3", The New England Journal of Medicine, vol. 370, No. 21, May 22, 2014, pp. 1993-2001.

Theraworx, "When Clean Is Not Enough", "Retrieved from the Internet:https://www.amemedbeds.com/pdf_files/brochure-theraworx.pdf", Aug. 1, 2014, pp. 7-8.

"Enterobacteriaceae (CRE)", Federal Register, vol. 80, No. 84, May 1, 2015, pp. 25169 (Total 30 pages).

International Search Report and Written Opinion received for PCT Application No. PCT/US2015/017151, dated Aug. 11, 2015, 7 pages.

International Search Report and Written Opinion received for PCT Patent Application No. PCT/US2015/61581, dated Jul. 18, 2016, 11 pages.

International Search Report and Written Opinion received for PCT Application No. PCT/US2016/038409, dated Sep. 21, 2016, 10 pages.

International Search Report and Written Opinion received for PCT Application No. PCT/US2016/038043, dated Sep. 27, 2016, 12 pages.

International Preliminary Report on Patentability received for PCT Application No. PCT/US2015/017151, dated Sep. 1, 2016, 6 pages.

International Preliminary Report on Patentability received for PCT Application No. PCT/US2015/061581, dated Jun. 1, 2017, 9 pages.

International Preliminary Report on Patentability received for PCT Application No. PCT/US2016/038043, completed on Nov. 2, 2017, 22 pages.

International Preliminary Report on Patentability received for PCT Application No. PCT/US2016/038409, completed on Oct. 31, 2017, 12 pages.

Department of Health and Human Services, "Safety and Effectiveness of Health Care Antiseptics; Topical Antimicrobial Drug Products for Over-the-Counter Human Use; Proposed Amendment of the Tentative Final Monograph; Reopening of Administrative Record", Federal Register, vol. 80, No. 84, May 1, 2015, pp. 25166-25205.

Ali et al., "Skin pH: From Basic Science to Basic Skin Care", Acta Dermato-Venereologica, vol. 93, Jan. 16, 2013, 9 pages.

Del Rosso et al., "The Clinical Relevance of Maintaining the Functional Integrity of the Stratum Corneum in both Healthy and Disease-Affected Skin", Journal of Clinical Aesthetic Dermatology, vol. 4, Issue 9, Sep. 16, 2011, 19 pages.

Marks, R., "The Stratum Corneum Barrier: The Final Frontier", American Society for Nutritional Sciences, 2004, pp. 2017S-2021S.

Response to Non-Final Office Action filed on May 21, 2001 for U.S. Appl. No. 09/471,538, dated Feb. 20, 2001, 20 pages.

\* cited by examiner

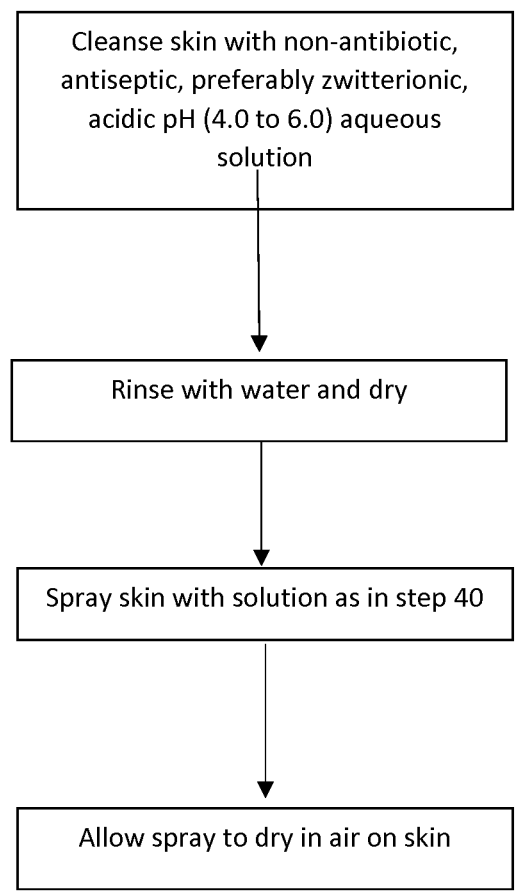

METHOD FOR THE PREVENTION AND TREATMENT OF ACNE

CROSS REFERENCE TO RELATED APPLICATION

This application claims the benefit of Woody U.S. Provisional Application Ser. No. 62/082,019 filed Nov. 19, 2014 and entitled Method for the Prevention and Treatment of Acne, the contents of which are incorporated herein by reference in their entirety.

FIELD OF THE INVENTION

This invention relates to the field of acne prevention and treatment, and more specifically to systems including methods and formulations used for reducing the occurrence and severity of various acne infections.

BACKGROUND OF THE INVENTION

Acne is an often chronic inflammatory disease of the sebaceous glands and is one the most common skin diseases on the plant, affecting at least 650 million people. Four out of five Americans between the ages of 12 and 24 develop at least one or more forms of acne, and scientists and dermatologists still struggle to explain the cause and to develop treatments. According to the American Academy of Dermatology, there are multiple forms of acne, ranging in severity from unsightly, bothersome, and common comedones, including blackheads, whiteheads, and pimples, to more serious problems that may include bacterial infections in papules, nodules, and cysts.

The sebaceous glands are typically located on the face, scalp, and back and secrete an oily or waxy substance called sebum that lubricates the hair and skin and improves barrier functions of the skin. A comedone is a basic acne lesion and occurs when a hair follicle becomes plugged with sebum and with skin debris, including dead skin cells. A blackhead occurs when the pore is open and the oil inside the pore is exposed to the air, oxidizes, and turns black. Blackheads vary in size and appear on the skin as black or grey spots. Whiteheads, which are not exposed to the air because the opening of the hair follicle is blocked with sebum and dead skin cells, appear as white bumps on the skin. The cosmetic industry has a number of remedies for extracting and removing blackheads and whiteheads, yet they often reoccur.

Another type of acne includes papules, which are comedones that have become inflamed and turn red. Pustules are a more severely infected type of inflamed pimple. The pustule is usually characterized by an inflamed bump that is filled with white or yellow pus. Severe forms of acne may also include cysts, which are large lesions that are pus filled and resemble boils. These more serious types of acne can lead to permanent scarring and even disfigurement.

Given the high occurrence of incidents of acne and the potential for serious consequences, medications and methods have been developed to reduce and combat acne breakouts. Medications have focused on three methods: 1) over-the-counter medications typically containing benzoyl peroxide or salicylic acid, in a topical delivery vehicle, including, for example, creams and gels; 2) topical retinoid prescription medications based on derivatives of Vitamin A and that may include the compounds tretinoin, which is a carboxylic acid of Vitamin A; tazarotene, which is a prodrug of the carboxylic acid of tazarotene; and adapalene, another topical retinoid; and 3) oral or topical prescription antibiotics including tetracycline and erythromycin among others. Although most of these compounds are capable of reducing the incidence of acne and some may also reduce the severity of an acne occurrence, each of them can have undesirable side effects, including adversely impacting the skin.

Salicylic acid and benzoyl peroxide can dry the skin and cause peeling and irritation of the stratum corneum, which is the highly differentiated outermost layer of the skin. Even more serious, the Food and Drug Administration (FDA) recently issued a Drug Safety Communication (DSC) to inform consumers and health care professionals of the potential dangers of certain acne products containing the active ingredients benzoyl peroxide or salicylic acid. The FDA warned that benzoyl peroxide and salicylic acid can cause rare, but serious and potentially life-threatening allergic reactions or severe irritation. The FDA warning was precipitated by the agency receiving reports from both consumers and manufacturers of allergic and hypersensitivity related adverse reactions associated with these over-the-counter (OTC) products. The reports contain incidents of throat tightness, shortness of breath, wheezing, low blood pressure, fainting or collapse.

Although the side effects of topical OTC products normally are listed on their labels, including a caution that if the side effects become too severe, the user should stop application and contact a physician, the FDA noted in their DSC that there is currently no mention of the possibility of very severe allergic reactions on the labels of acne products containing benzoyl peroxide and salicylic acid.

Prescription topical medications used for the treatment of acne typically are much more powerful than topical OTC medications, and they can also cause very serious incidents of skin drying, flaking, and redness. Sunscreen may be required because some OTC's increase sensitivity to sunburn. Prescription topical medications for the treatment of acne containing tazarotene can cause serious birth defects. Women are cautioned to avoid having children while prescribed drugs containing tazarotene.

Prescription antibiotics can be used to treat acne. However, concerns exist among many that antibiotics are overused, causing increases in antibiotic resistance, which means that the antibiotics are less effective at killing or controlling the bacteria that causes acne, as the bacteria can become resistant to the antibiotic.

Generally speaking, it is recognized that treatments that adversely impact the skin, and including the outermost layer, the stratum corneum, which is a complex organ of many functions, need to be improved. For example, Marks, R., in "The Stratum Corneum Barrier: The Final Frontier," published in 2004 in the American Society for Nutritional Sciences, pages 2017S through 2021S, notes that healthy stratum corneum is highly efficient in its multiple barrier functions at restricting the movement of water in and out of the body and in precluding penetration of chemical agents. Damaged stratum corneum is said to be capable of losing up to 6 liters of water per day by transepidermal water loss and may allow ingress of chemical agents and pathogens.

Formation of the outer layer of the epidermis is a complex process often referred to as "keratinization." Keratinization is characterized by, among others, water loss and a reduction in pH from the inner to outermost stratum corneum layer, the development of thin overlapping horn cells called corneocytes, specialized cross-linked proteins that are highly chemical resistant, and specialized non-polar lipids that provide a water barrier property. The constant outward movement of corneocytes to be sloughed off at the surface in the process of an orderly desquamation of individual keratinized cells is said to be a built-in mechanism to preclude pathogens from gaining a foothold. Impairment of desquamation, as when the binding force between corneocytes increases under stress and causes the cells to desquamate in clumps, is often characterized as scaling, as in eczema and psoriasis.

Treatments that interfere with the processes of keratinization and desquamation of the stratum corneum inevitably damage the stratum corneum functions, including water and chemical barrier functions, promoting scaling, redness, and pruritus, and decreasing flexibility.

Ali, S. M. and Yosipovitch, G. in "Skin pH: From Basic Science to Basic Skin Care," published Jan. 16, 2013 in Vol. 93 of Acta Dermato Venereologica at pages 261 to 267, posits generally that in managing skin diseases including acne, use of soaps and creams that do not compromise the acidic pH of the skin should become part of the treatment regimen and that the ideal cleanser has a pH of between 4.5 and 6.5, similar to normal skin. Frequent use of alkaline soaps is said to cause irritation and the article discloses the desirability of preserving or restoring an acidic milieu by using agents compatible with the acid mantle to restore barrier function when the barrier function is faulty. However, no specific alternative cleansers or treatments are recommended for any particular skin disease and there is little data confirming an innate impairment of the stratum corneum permeability barrier in *acne vulgaris*. See, Del Rosso, J. Q. and Levin, Jacqueline, "The Clinical Relevance of Maintaining the Functional Integrity of the Stratum Corneum in both Healthy and Disease-affected Skin," published September 2011 in the Journal of Clinical Aesthetic Dermatology, Vol. 4, issue 9, at pages 22 to 42.

It would be desirable to develop specific alternative methods and products for reducing the incidence and severity of one or more forms of acne that do not have or at least reduce the drawbacks associated with the above-described prevalent treatments and products.

SUMMARY OF THE INVENTION

This invention relates to improvements in systems, including methods and formulations for treating and reducing the frequency and severity of incidences of acne on the organ of the skin. The system of the invention effectively cleanses and exfoliates the skin of dead skin cells, skin debris, and excess sebum, in the absence of exposing higher pH and lower layers of skin and while promoting an orderly desquamation of individual cells, preserving specialized lipid components, and maintaining normal exterior-most mildly acidic skin pH over an extended period of time. Practice of the steps of the system over time maintains or restores the skin's naturally occurring acidic mantle, reduces bacterial growth, promotes the skin's natural defense resources, promotes healing of existing acne lesions, and precludes or at least reduces the severity of new acne lesions. The system obtains these results by promoting three different abilities of useful treatment substances: promoting antimicrobial properties in the absence of damaging the stratum corneum of the skin, promoting healing of existing acne wounds, and creating a zone of inhibition to preclude the formation of new acne lesions. Each of these functions can be performed by a single solution formulated to be non-antibiotic, antimicrobial, mildly acidic, and zwittterionic when used for cleansing, and the invention is based in part on the surprising recognition that solutions meeting these parameters have remarkable effectiveness on acne in the absence of the problems associated with the armamentarium of the prior art.

The system of the invention normally includes in a 24-hour period the method steps of 1) cleansing the skin with a suitable substance as described below, rinsing the skin with water, and drying the skin; 2) applying the substance to the skin and allowing the substance to dry in air and remain on the skin; 3) repeating step (2) at selected intervals of applying the substance to the skin and allowing it to remain in contact with the skin; and 4) repeating step (1). For example, in a specific embodiment, step (1) is accomplished in the morning on arising; step (2) is accomplished immediately after step (1); step (3) is repeated at selected intervals of from 3 to 6 hours throughout the day following step (2); and step (4) is accomplished in the evening on retiring. Of course, depending on one's schedule, steps (1), (2), and (3) may be performed in the evening and step (4) the following morning. Steps (1) and (4) alone may be sufficient in some instances. In alternative embodiments, the steps may be repeated for as long as desired to prevent acne or reduce its likelihood and severity when it does occur, or the steps may be applied directly to acne lesions for as long as needed to improve the condition of the skin.

In sharp distinction to the prior art, the substance applied to the skin in the practice of the system of the invention does not typically have adverse side effects. Many of the prior art compounds may be capable of reducing the incidence and severity of acne, but these compounds also tend to damage the skin in one or another ways that may actually contribute to subsequent infections, promoting the recurrence of acne. One specific way these prior compounds damage the skin is by damaging the stratum corneum, which is the outermost layer of the skin and is a highly differentiated, complex layer. The ingredients in many anti-acne topical creams, gels, and sprays are reported to dry the skin and cause flaking or redness, damage the mantle, or otherwise increase the pH of the skin to basic levels at which bacterial growth may be promoted.

The substance applied to the skin in the practice of the invention typically will be a liquid solution and may be dispersed in a gel, foam, or cream, which promotes a mildly acidic pH of from about 4.5 to 5.5 over an extended period of time, is antimicrobial, or at least antiseptic, and does not remove beneficial lipids, thus preserving the integrity of the skin while reducing the opportunity for infection or inflammation of acne wounds. The substance may be applied via any convenient vehicle. For example, the substance may normally be applied as a liquid or foam cleansing solution in the morning and evening, typically a liquid or foam having surfactants incorporated for cleansing, and may be applied as ingredients in a spray, the spray often incorporating a toner having some astringent quality. The spray may or may not incorporate surfactants.

It is not sufficient that the solution simply be of an appropriately acidic pH. On the contrary, the solutions used will all typically be non-antibiotic, zwitterionic, antimicrobial, or at least antiseptic, and of mildly acidic pH of from 4.0 to 6.0 overall. Surfactants normally are included for cleansing to avoid stripping beneficial lipids from the skin. Astringent "toners" may be included for sprayed and dried-on-the-skin steps of the method, which may or may not include surfactants. Soaps normally are not included.

In addition to pH maintenance of the stratum corneum in a mildly acidic state, in combination with the non-antibiotic, zwitterionic, antimicrobial, or at least antiseptic, properties of the solution used in accordance with the invention, the method of the invention may employ compounds in a solution that do not in themselves strip the skin of lipids or moisture, which allows the skin to maintain normal functions, and not hinder desquamation of dead skin cells. It is believed that typical cleansers and prior art acne treatments allow the skin to lose moisture and lipids. Although initially drying the skin, loss of moisture and lipids in the long run increases sebum production and can make the acne condition worse over time. Prior art products and treatments that develop a basic environment on the skin are believed to contribute to bacterial infection by promoting bacterial growth and may damage of the stratum corneum barrier and moisture transport functions.

The pH of the cleansing solution and spray used in the practice method of the invention is acidic, and should not be so low as to be painful on application nor so high as to promote infection. A preferred suitable range of pH is from about 4.5 to 5.5 with the ability of the solution to maintain or develop a suitable acidic pH on the skin for an extended period of time, even as applied to infected acne lesions, which may be more basic in nature as a result of the proliferation of bacteria. The solution is wound compatible, and does not irritate the wounds and lesions associated with acne, and assists in wound healing. The solution preferably is zwitterionic so as not to strip naturally occurring and protective lipids from the skin, allowing the skin to stay hydrated, although capable of removing excessive oils, especially sebum. The solution may also be, but is not required to be, antimicrobial or at least antiseptic, and will typically be non-antibiotic. It is especially useful that the solution is capable of maintaining the balance of flora associated with normal skin, even as the acne flora is reduced, by creating a zone of inhibition in which acne bacteria cannot grow. The zone of inhibition is a complex phenomenon that includes not only a lower pH to inhibit bacterial growth, but orderly desquamation to preclude bacterial infection, and a normal moisture transpiration to preserve flexibility and integrity of the skin. It is also desirable that the solution be easily absorbed through the epidermis and at least into the deep layers of the dermis to assist in the healing of the wounds created by acne infections.

Thus, the invention provides an easily implemented system including method steps and formulations for the prevention and treatment of acne, including the steps of cleansing the skin with a solution as described upon arising and rinsing the cleansed skin with water; immediately applying the solution to the skin, typically in the form of a spray toner, and allowing the toner to dry on the skin in contact with air; repeating this immediately previous step at least once or twice and up to about eight times per day; and cleansing the skin with a solution as described upon retiring and rinsing the cleansed skin with water. Optionally, the solution may be sprayed on and allowed to air dry thereafter for bedtime, and the entire sequence may be repeated on subsequent days for a period of time to demonstrate the desired results.

A suitable solution for use in the practice of the method steps of the invention, meeting the parameters as above described, and available as a liquid, spray liquid, and foam, is THERAWORX® brand skin cleanser available from Avadim Technologies, Inc. in Asheville, N.C. THERAWORX® brand skin cleanser and similar skin cleansers are described in U.S. Pat. No. 6,358,516, the contents of which are incorporated herein by reference in their entirety.

BRIEF SUMMARY OF THE DRAWINGS

Having described the invention in general terms, reference will now be made to the accompanying drawing, wherein:

FIG. 1 illustrates generally an embodiment of the method steps used in the practice of the invention as described in the detailed description below.

DETAILED DESCRIPTION

The invention will now be fully described more fully hereinafter with reference to the accompanying FIG. 1 in which are illustrated some, but not all, of the concepts of the invention. Indeed, the invention maybe embodied in many different forms and should not be construed as limited to the specific embodiments set forth herein; rather, the embodiments provided in this disclosure are intended to satisfy applicable legal requirements.

In the first step of the practice of the method of the invention, which is step number 40 in FIG. 1, a skin cleansing solution with a pH from about 4.5 to 5.5 is applied to an area of the skin. Step 40 comprises massaging the cleansing solution into the skin. The area of skin selected may be where one desires to prevent acne lesions or may be skin with acne that one wishes to restore to an acne-free condition or at least having substantially reduced acne lesions. The cleanser acts to remove cellular debris, including dirt, dead skin cells, excess sebum, and the many types of bacteria found on the skin, including among others *Acne vulgaris*, and *Propionibacterium acnes*. Typically, the cleanser will be delivered in a standard method such as, a gel, foam, cream, or liquid, but it is not limited to these types exclusively. Normal skin has a slightly acidic pH that ranges from 4.0 to 6.5. It is important to note that the cleansing solution can be produced at pH's from 4.0 to 6.5, if preferred. The acidic environment maintained by the skin helps to inhibit bacteria and other flora from growing on the skin. A somewhat lower pH may be selected initially, from about 4.0 to 4.5 or 5.0 to promote healing of infected lesions.

To maintain skin health, it is important to cleanse regularly without disrupting the skin's naturally occurring acidic mantle. The acid mantel is vital to the integrity of the stratum corneum and key component of a healthy stratum corneum is maintaining the normal pH range of skin. A cleanser is preferred that can cleanse the skin without damaging the skin's acid mantle or introducing harmful irritants to the skin, but still have antimicrobial properties. It is also important that the cleanser not interfere with normal desquamation of cells or strip complex lipids from the stratum corneum that are used by the skin to control moisture transport or promote a basic pH.

Products that are placed on the skin can directly impact the skin's pH. For example, when many prior art cleansers, which typically are quite alkaline with a pH above 7.0, are applied directly to an acne lesion or to clear skin, these cleansers can strip the skin of its acidic layer that helps prevent bacterial growth. Without this acidic layer protecting the skin, the bacteria responsible for some forms of acne, can flourish. Cleansing with the solution as described in detail herein below, initiates restoration and maintenance of the skin's natural acidic barrier.

Following the application of the cleanser in step 40 to the affected area, the cleanser should be rinsed with water as illustrated in the following step 45. The cleansing solution may be rinsed with water directly applied to the skin or using a water-soaked clean cloth to assist in removal of the solution. Removing the cleansing solution also assists in removing the loosened cellular debris and excess sebum that the solution has dislodged from the pores and skin surface during the cleansing process. However, rinsing with water drives the pH to 7.0 and so, although rinsing is an important last step in cleansing, the solution should be reapplied, normally in the absence of surfactants, preferably by spraying, perhaps as a toner, and allowed to dry on the skin.

After the skin has been thoroughly cleansed without disturbing the natural pH of the skin or its lipids or proteins, or otherwise adversely impacting the integrity of the skin, it is important to lower the pH on the skin that exhibits acne lesions or is prone to acne lesions to promote the healing process and restore the skin to normal functioning. Infected skin typically exhibits a more basic pH that promotes bacterial growth, and reducing the pH to an acidic level improves oxygenation of the wound, allows existing acne wounds to heal, and can reduce or even eliminate formation of new acne sites. After the skin function is restored, continual application of the solution at the correct pH keeps the barrier function of the skin intact.

After the rinse is complete as in step 45 and the skin has been thoroughly cleansed, the skin typically is dried with a towel. Thereafter, in accordance with the next step 50, the solution may be sprayed directly on the area previously cleansed as in step 40 to promote healing by lowering the pH. For example, a "toner" including mildly astringent substances may be used for this purpose. The toner can be applied in step 50 to the skin by spraying it on the skin directly or by saturating a cotton pad with the toner and then wiping the toner over the skin. Once the toner has been applied, it should be allowed to air dry as in step 55, and not rinsed off of the skin. This is because the toner solution, similar to the cleansing solution used in step 40, has a pH from about 4.5 to 5.5, or alternatively, from about 4.0 to 6.5. The combination of cleansing, rinsing, and toning assists in maintaining the pH of the skin in the area where the solution is applied at a value of from 4.5 to 5.5 for an extended time of up to three to six hours per application, thereby maintaining the skin's acidic mantle which helps to create a zone of inhibition that limits the growth of bacteria. Depending on the specific formulation and the severity of infection, the solution pH can be extended to from about 4.0 to 6.5. The use of the formulations in the method of the invention assists the skin in achieving and maintaining normal moisture content and mildly acidic pH, enabling normal sebum production and exfoliation of skin debris.

Steps 50 and 55 may be repeated as desired as illustrated in step 60, typically up to 3 to 5 times daily or even up to 8 times, to maintain pH, to fight bacterial growth, and to promote normal skin function. The pH of the skin will normally vary by individuals during the day. On retiring, steps 40 and 45 are repeated and immediately thereafter an initial sequence of steps 50 and 55 may be included until the following day when steps 40 through 65 are repeated as described above.

Thus, the practice of the invention promotes wound healing of acne lesions in part by modulating the pH of the acne site through cleansing the skin, restoring the skin, and protecting the skin.

In one embodiment of the invention, the cleansing solution is applied upon arising, step 40, and rinsed off with water, step 45; toner solution is applied via spray step 50 and the sprayed toner is allowed to air dry, step 55. The procedure of applying the toner, step 50, via spray and air drying, step 55 could be repeated up to 3 or 4 times daily, step 60, or more frequently. Then, before retiring for the day, the cleansing and rinsing steps 40 and 45 may optionally be repeated. Immediately thereafter, a toner solution or other application of the solution is sprayed on the skin, step 50 and allowed to dry as in step 55 so the product remains on the skin until arising again. On arising, steps 40 through 65 are repeated as described, and daily for a time sufficient to treat or prevent the acne lesions.

In an alternative embodiment, the skin can be cleansed and rinsed only once per day with the solution, steps 40 and 45, and a solution applied at least once and allowed to air dry before retiring, steps 50 and 55. Typically, during the time between the first cleansing of the day and the application and drying of solution at the last of the day, the solution will be applied and allowed to dry multiple times, at least three or four. Each embodiment allows for the area to be treated by continual use on a daily basis, thereby achieving an optimized pH level of from 4.5 to 5.5, inhibiting bacterial growth, removing cell debris and excessive sebum, and restoring normal function to the skin.

Turning now to a discussion of the skin's acid mantle, maintaining the effectiveness of the acid mantle promotes good skin health. A damaged acid mantle may lead to a number of skin complaints, such as, dry skin, flaky skin, oil overproduction, sensitivity, and acne. Products that do not facilitate the skin's natural pH can contribute to the degradation of the acid mantle, thereby increasing the likelihood that acne can develop and cause related lesions and wounds. When the acid mantle is damaged, it can take up to 14 to 17 hours to repair itself, and it is during this time that bacteria can be expected to multiply more effectively. Thus, skin pH is an important component of effectively treating acne. Practice of the invention and continual adherence to its method to maintain the skin's pH is recommended to reduce and prevent the occurrence and severity of incidents of acne on the face and body.

The skin is the largest organ in the human body and is comprised of three primary layers: the epidermis, which is the outermost layer; an intermediate layer, the dermis, comprising hair follicles, pores, sebaceous glands, sweat glands and connective tissue; and the hypodermis, which comprises an insulating fatty layer. The outermost layer, the stratum corneum (SC), is exposed to conditions such as, temperature and humidity as well as various hygienic, cosmetic, and other personal care products that can cause damage to this layer. The resulting damage often causes drying of the SC, which can cause the SC to crack, interfere with the normal shedding of skin cells, and prevent the natural healing of damaged cells. The SC comprises dead skin cells and forms an important barrier layer protecting the underlying tissue from infection, dehydration, chemicals, and abrasion. However, when dead skin cells and cellular debris are not successfully desquamated, and become trapped within a pore, an acne wound is the result. Bacteria can proliferate in the anaerobic environment of the plugged pore, resulting in infection of the wound.

Solutions that are used in connection with treating acne should typically preserve the barrier function of the skin, components of which are an acidic pH and sustained moisture content, in addition to optionally having antimicrobial properties that address the many types of bacteria that can cause acne. The acidic pH of the skincare solution used in the practice of the method of the invention can vary from as low as 4.0 to as high as 6.5, which is the range of natural, uninfected skin. The solution is preferably zwitterionic so as not to strip the naturally occurring and protective lipids from the skin, therefore allowing the skin to stay hydrated. The solution may also be, but is not required to be, antimicrobial or at least antiseptic, and will typically be non-antibiotic, unnecessary antibiotic use contributing to resistance in bacteria strains. It is especially useful if the solution is capable of maintaining the balance of flora associated with normal skin, even if the quantity of flora is somewhat reduced. It is also desirable that the solution be easily absorbed through the epidermis and at least into the deep layers of the dermis in the absence of creating micro-abrasions that can provide an entry point for infectious agents.

It is thus desirable to use less harsh antimicrobial or antiseptic compounds that do not damage the skin, that promote a pH level similar to that of normal skin, and that preserve moisture and lipids to restore skin function, including sebum production and desquamation of cellular debris. Cleansing and toning can be accomplished in accordance with the method steps of the invention using a variety of skincare solutions. One aqueous skincare solution that is effective in the practice of the invention is THERAWORX® brand skin cleanser and similar skin cleansers available from Avadim Technologies, Inc. in Asheville, N.C. THERAWORX® brand skin cleanser and similar skin cleansers are described in U.S. Pat. No. 6,358,516, the contents of which are incorporated herein by reference in their entirety.

Humectants and emollients and agents for promoting healing as taught in U.S. Pat. No. 6,358,516 are desirable. A skincare and cleansing agent useful in the practice of the invention may include, among other ingredients:

(a) at least one surfactant for cleansing functions;
(b) at least one anti-inflammatory;
(c) at least one anti-foaming agent;
(d) at least one cell growth-promoting agent;
(e) at least one fast-acting antimicrobial agent, each of said ingredients being skin-compatible and different from the other ingredients of said composition; and at least one different ingredient selected from the group of:
(f) immune system-enhancing agents, wherein at least one immune system-enhancing agent is aloe vera, beta glucan, colloidal silver, or allantoin;
(g) absorption facilitation agents, where in at least one absorption facilitating agent is beta glucan, aloe vera, or colloidal silver;
(h) humectants and emollients, wherein at least one humectant or emollient is aloe vera, vitamin E, or cocamidopropyl;
(i) free radical-scavenging agents, wherein at least one free radical-scavenging agent is a bioflavonoid, a polyphenolic compound, a grapefruit-derived quaternary compound, beta glucan, allantoin, vitamin E, pycnogenol, or grape seed extract; and
(j) healing promoting agents, wherein said ingredients are selected to form a stable, no-rinse, radiation-sterilizable composition that air-dries quickly when applied to the skin and that cleanses, therapeutically conditions, and treats the skin in a one-step application, wherein the at least one healing-promoting agent is aloe vera, allantoin, or beta glucan.

It should be recognized that where a compound is mentioned in two different categories that the compound serves both functions in the formulation and that each function is present when the compound is present.

Cleansing agents, such as those suitable for use in step 40 of the invention, include surfactants, such as, soaps but not limited to, amphoteric surfactants, which are surfactants having the capacity of behaving either as an acid or a base, including, for example, cocamidopropyl betain, alkyl polyglucosides, lauryl glucoside, and combinations thereof.

Reddened skin is the first sign of an infection and other skin problems, and indicates that the skin is redirecting its natural resources from growth and other normal functions to prevention and repair. Reducing or eliminating reddening may increase the growth of healthier new skin. Anti-inflammatory agents include agents that are known to reduce skin reddening, including, but not limited to aloe vera, allantoin, cocamidopropyl betain, beta glucan, and combinations thereof, in amounts shown to be effective during cleansing. Skin-compatible anti-foaming agents include silicone-based antifoaming agents, dimethicone copolyol, and the like.

When present in the preferred combinations and concentrations, growth-promoting agents promote or stimulate new skin growth and promote healing of significantly greater magnitude than previously observed. Agents that stimulate or promote cell growth, include, but not limited to, aloe vera, allantoin (glyocyldiureide; 5-ureidohydantoin), beta glucan, polyphenolic compounds such as CITRICIDAL® brand grapefruit-derived quaternary compound, and combinations thereof. CITRICIDAL® brand grapefruit-derived quaternary compound and the like compounds have been demonstrated to be effective against a broad spectrum of bacteria. These compounds contain quaternary moieties derived from grapefruit or other bioflavonoids together with inert ingredients, including glycerin.

Agents that enhance and/or stimulate the skin's immune system and/or help provide a secondary immune system, include, but are not limited to, aloe vera, beta glucan, colloidal silver, allantoin, and combinations thereof. When present in the solution composition in the preferred quantities, these agents promote healing and also help reduce the incidence of infections, such as acne. Some of these substances may also enhance the skin's natural barrier function. Solutions that meet these criteria and may also be used in the system and method of the invention, although not necessarily with equivalent results, may also be described in International Patent Application No. PCT/US2013/032535, which was published Sep. 26, 2013 as WO 2013/142374, the contents of which are incorporated herein by reference, to the extent the solution is antiseptic, mildly acidic, and non-antibiotic, and that for cleansing functions zwitterionic surfactants are employed to avoid stripping lipids. The solutions are aqueous mixtures of synthetic, cationic polypeptides with antimicrobial activity with 10% by weight of the synthetic and cationic polypeptide comprising at least one pharmaceutically acceptable polymer that is not synthetic, cationic polypeptide, each present in at least about 100 µg/mL based on total aqueous volume and each mutually miscible in water.

Colloidal silver, CITRICIDAL® brand grapefruit-derived quaternary compound, beta glucan, aloe vera, and like ingredients promote and/or stimulate the existing immune system to help reduce infections and promote healing. Colloidal silver and CITRICIDAL® brand grapefruit-derived quaternary compound support the natural immune system by reducing its workload; CITRICIDAL® brand grapefruit-derived quaternary compound is also believed to promote healing by a mechanism which is yet unclear.

Beta glucan, which is a D-glucose polymer also known as beta-1 extract or yeast derivative, is a non-specific immune stimulator that also exhibits free-radical scavenging activity. Beta glucan stimulates the body's immune system T-cells; mannoproteins and polysaccharides such as aloe vera assist the T-cells effectiveness. A mannoprotein is a sugar-protein, a glycoprotein that is linked to beta glucan in yeast and barley cell walls. Mannoproteins directly increase the structural integrity, alertness and numbers of immune cells. Fast-acting, skin-compatible antimicrobial agents are effective against at least one or all of bacteria, viruses, yeasts, and fungi, and include, but not limited to colloidal silver, CITRICIDAL® brand grapefruit-derived quaternary compound, pycnogenol, grape seed extract, antibiotics, and combinations thereof, in effective amounts to kill infectious organisms, including bacteria, but also viruses, yeasts, and fungi on and in the skin during skin cleansing and upon drying.

The skin harbors a wide variety of microorganisms; some of these are potentially harmful while others are beneficial. Ideally, this normal bacterial flora is not destroyed by cleansing. However, a cleanser that reduces the accumulation of bacteria and fungi present on the skin helps reduce the incidence of skin infections. The selected antimicrobial agent or agents is fast-acting, so as to act against bacteria, and the like microorganisms. The action of the antimicrobial agent or agents during cleansing and rapid air drying substantially kills viruses, bacteria, fungi, and yeasts present in the living basal cell layer and the dermis of the skin in addition to those transferred onto or living in the dead horny layer or epidermis. This action serves to reduce the occurrence or severity of infections due to bacteria, viruses, and the like infectious microorganisms entering breaks in the skin, whether small tears or micro abrasions.

Some antimicrobial agents, such as colloidal silver and CITRICIDAL® brand grapefruit-derived quaternary compound, are compatible with normal flora, capable of penetrating into the dermis, and also provide useful antimicrobial properties. Colloidal silver kills single cell microorganisms such as bacteria by penetrating their cell walls in a manner similar to the body's T-cells. Therefore, these organisms cannot mutate into resistant strains as they do with many other antimicrobial agents. However, colloidal silver has limited potency and must preferably be supplemented with other antimicrobial agents in formulating a composition according to the invention. In addition, the colloidal silver is preferably formulated with particles that are small enough to penetrate the dermis (approximately 0.005-0.02 microns; more preferably, approximately 0.01-0.1 microns).

Compatible humectants and emollients, including but not limited to aloe vera, allantoin, vitamin E (tocopherol), beta glucan, cocamidopropyl betain, and combinations thereof. These agents naturally re-moisturize the dead horny layer, epidermis, and/or dermis without clogging pores. Humectants and emollients in the composition act to naturally remoisturize the skin surface (i.e., the dermis) to prevent dryness, increase elasticity, reduce the incidence of skin tears, and supplement the activity of the sebaceous glands to reproduce oils without clogging pores. Over usage of humectants and/or emollients is a major cause of skin eruptions, inflammation, and acne, therefore, simply increasing the amounts of humectants and/or emulsifiers to provide a longer lasting protective barrier can promote skin problems. Therefore, the amounts of these ingredients are controlled so as to minimize undesirable effects.

Agents that scavenge free radicals and help detoxify the skin, include, but are not limited to CITRICIDAL® brand grapefruit-derived quaternary compound, beta glucan, allantoin, vitamin E, pycnogenol, grape seed extract, and combinations thereof. Agents that promote and/or stimulate new skin growth and skin healing, including but not limited to include, but are not limited to aloe vera, allantoin, CITRICIDAL® brand grapefruit-derived quaternary compound, beta glucan, pharmaceuticals, and combinations thereof. Biocompatible preservatives, including but not limited to methylparaben, propylparaben, ethylenediaminetetraacetic acid (EDTA), like agents, and combinations thereof. Biocompatible fragrances, including but not limited to natural orange, lemon, lavender, and combinations thereof. Other beneficial agents, including but not limited to those containing vitamins and vitamin precursors (vitamin A, carotene, cryptoxanthin, retinol, 3-dehydroretinol, vitamin C (absorbic acid), vitamin E (tocopherol), etc.), herbs (chamomile, lavender, ginseng, ginkgo, etc.), antioxidants, collagens, pH-balancing agents, and combinations thereof. Each ingredient of the composition is present in an amount that, as a percentage of the total weight of the composition, is effective either alone or synergistically with the other ingredients to achieve the desired results.

To exemplify the method of the invention as described above, THERAWORX® brand skin cleanser was applied in vitro to *Propionibacterium acnes* and the effectiveness of the THERAWORX® brand skin cleanser formula to kill the organism was measured after various intervals of time. The results demonstrate that after fifteen (15) minutes of exposure to the formulation, the number of viable bacterial cells, as measured by colony forming units per milliliter ("CFU/ml"), was reduced to less than 10 units. Total log reduction in viable *Propionibacterium acnes* was 4.839. A log reduction of 6.0 is considered sterile. Thus, for the treatment of acne, the formulation as applied can be expected to provide near sterile conditions. The table below illustrates the results of the testing.

TABLE 1

Log Reduction in *Propionibacterium acnes*

| Time Tested | Replicate #1 CFU/mL | Replicate #2 CFU/mL | Log Reduction |
| --- | --- | --- | --- |
| 15 minutes | <10 | <10 | 4.839 |
| 30 minutes | <10 | <10 | 4.839 |
| 60 minutes | <10 | <10 | 4.839 |
| 120 minutes | <10 | <10 | 4.839 |
| 180 minutes | <10 | <10 | 4.839 |

T = 0 Positive Control: $6.90 \times 10^5$ CFU/mL

It should be recognized that a variety of solutions may be devised and delivered in a variety of vehicles to achieve the ends of the invention, namely, to cleanse, restore, and protect the skin so that acne is prevented or the incidence of its occurrence and severity is reduced. These solutions include surfactants for cleansing and are acidic and capable of maintaining an acidic condition of the skin when applied in the method of the invention, modulating the pH throughout each of the phases of acne prevention and treatment.

What is claimed is:

1. A method for reducing the incidence and severity of acne disease on human skin by
   a. applying an acidic solution to the surface of the skin to cleanse the skin by loosening and removing skin debris and sebum, wherein the solution comprises an aqueous composition comprising at least one surfactant agent for cleansing the skin selected from the group consisting of cocamidopropyl betain, alkyl polyglucosides, lauryl glucoside, and combinations thereof; at least one anti-inflammatory agent selected from the group consisting of aloe vera, allantoin, cocamidopropyl betain, beta glucan, and combinations thereof; at least one cell growth promoting agent selected from the group consisting of aloe vera, allantoin, beta glucan, a bioflavonoid, a polyphenolic compound, or a grapefruit-derived quaternary compound and combinations thereof; and at least one fast acting antimicrobial agent selected from the group consisting of colloidal silver, a bioflavonoid, a polyphenolic compound, or a grapefruit-derived quaternary compound and combinations thereof, wherein each of said agents is skin-compatible and different from the other agents; and at least one different agent selected from the group consisting of aloe vera, beta glucan, colloidal silver, allantoin, vitamin E, cocamidopropyl, a bioflavonoid, a polyphenolic compound, a grapefruit-derived quaternary compound, pycogenol, and grape seed extract, the solution having a pH of from about 4.0 to 6.0, and promoting an orderly desquamation of individual cells, preserving specialized lipid components, and maintaining normal exterior-most mildly acidic skin pH of from about 4.0 to 6.5 over an extended period of time from about 3 to 6 hours;

b. thereafter applying an acidic solution as described in subparagraph (a) having a pH of from about 4.0 to 6.0 and in the absence of surfactants to the surface of the skin and allowing the solution to dry in air to restore the barrier function of the skin, promote healing, and reduce the likelihood of bacterial infection;

c. repeating step (b) from 3 to 8 times per day; and d. repeating step (a).

2. The method of claim 1 wherein step (a) is performed upon arising, step (b) is performed immediately after step (a) is completed, step (c) is repeated throughout a 24 hour period, step (d) is performed upon retiring, and steps (a) through (d) are repeated daily for a period of time from 1 to 4 weeks.

3. A method for reducing the incidence and severity of acne on human skin by applying an antimicrobial and pH controlling solution to the skin, the solution comprising an aqueous composition of at least one anti-inflammatory agent selected from the group consisting of aloe vera, allantoin, cocamidopropyl betain, beta glucan, and combinations thereof; at least one cell growth promoting agent selected from the group consisting of aloe vera, allantoin, beta glucan, a bioflavonoid, a polyphenolic compound, or a grapefruit-derived quaternary compound and combinations thereof; and at least one fast acting antimicrobial agent that is not also antibiotic the fast acting antimicrobial agent selected from the group consisting of colloidal silver, a bioflavonoid, a polyphenolic compound, or a grapefruit-derived quaternary compound and combinations thereof, wherein each of said agents is skin-compatible and different from the other agents; and at least one different agent selected from the group consisting of aloe vera, beta glucan, colloidal silver, allantoin, vitamin E, cocamidopropyl, a bioflavonoid, a polyphenolic compound, a grapefruit-derived quaternary compound, pycogenol, and grape seed extract, the solution having a mildly acidic pH of from about 4.0 to 6.5, wherein the method comprises the steps of:

a) cleansing the skin at least once per day with the solution, the solution further comprising at least one zwitterionic surfactant to cleanse the skin by loosening and removing skin debris and sebum while preserving lipid components;

b) rinsing the solution from the skin with water after the cleansing step; and c) applying the solution to the skin after rinsing and allowing the solution to air dry on the skin, the solution further comprising or not at least one zwitterionic surfactant; the method further comprising the step of:

d) repeating at least step (c) as needed for a period of time sufficient to maintain exterior-most acidic skin pH of from about 4.0 to 6.5 in the area of application over an extended period of time from about 3 to 6 hours, thereby establishing a zone of inhibition for infection, restoring skin function characterizing healthy human skin, and reducing the incidence and severity of acne within the area of application, healthy human skin characterized by a pH of from about 4.0 to 6.5; keratinization, including corneocyte development, cross-linked proteins, and non-polar lipids; and desquamation of individual keratinized cells.

4. The method of claim 3 wherein the solution has a pH of from about 4.5 to 6.0.

5. The method of claim 3 wherein the solution has a pH of from about 4.5 to 5.5.

6. The method of claim 3 wherein the acne includes lesions inflamed with acne causing bacteria.

7. The method of claim 3 wherein the solution maintains the pH of the area to which the solution is applied at from 4.0 to 4.5 for an extended time of up to three to six hours per application.

8. The method of claim 3 wherein step (c) of applying the solution to the skin and allowing the solution to dry in air on the skin is accomplished from 3 to 8 times per day following an initial single cleansing and rinsing, steps (a) and (b), and wherein the method further comprises repeating steps (a) through (c) before retiring.

9. The method of claim 3 further comprising the step of drying the rinsed skin after step (b) and prior to step (c).

10. The method of claim 3 wherein step (c) is repeated multiple times per day.

11. The method of claim 3 wherein steps (a) through (c) are repeated at least twice per day.

12. The method of claim 11 wherein step (c) is repeated multiple times per day in between the repetition of steps (a) through (c).

13. The method of claim 3 wherein rinsing in accordance with step (b) is performed with water or with a cloth having water applied thereto.

14. The method of claim 3 wherein step (c) is performed by applying the solution in the absence of a zwitterionic surfactant.

15. The method of claim 3 wherein the antimicrobial agent is selected from colloidal silver, grapefruit-derived quaternary compound, and mixtures thereof.

* * * * *